United States Patent
Dreyfuss (10) Patent No.: US 7,585,305 B2
(45) Date of Patent: Sep. 8, 2009

(54) SUTURE PASSING INSTRUMENT

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 459 days.

(21) Appl. No.: 10/428,072

(22) Filed: May 2, 2003

(65) Prior Publication Data

US 2003/0233106 A1 Dec. 18, 2003

Related U.S. Application Data

(60) Provisional application No. 60/380,302, filed on May 15, 2002.

(51) Int. Cl.
A61B 17/04 (2006.01)

(52) U.S. Cl. .................................................... 606/144

(58) Field of Classification Search ................. 606/139, 606/144, 148
See application file for complete search history.

(56) References Cited

U.S. PATENT DOCUMENTS

| 1,856,721 | A | * | 5/1932 | Nagelmann | ................. | 606/145 |
| 4,441,497 | A | | 4/1984 | Paudler | | |
| 4,781,190 | A | | 11/1988 | Lee | | |
| 4,890,615 | A | | 1/1990 | Caspari et al. | | |
| 5,254,126 | A | * | 10/1993 | Filipi et al. | ................. | 606/146 |
| 5,318,579 | A | * | 6/1994 | Chow | ......................... | 606/148 |
| 5,417,701 | A | * | 5/1995 | Holmes | ...................... | 606/148 |
| 5,454,823 | A | * | 10/1995 | Richardson et al. | ......... | 606/148 |
| 5,730,747 | A | * | 3/1998 | Ek et al. | ..................... | 606/148 |
| 5,824,009 | A | | 10/1998 | Fukuda et al. | | |
| 5,895,393 | A | * | 4/1999 | Pagedas | ...................... | 606/139 |
| 5,947,982 | A | | 9/1999 | Duran | | |
| 6,638,283 | B2 | * | 10/2003 | Thal | ........................... | 606/144 |
| 7,112,208 | B2 | * | 9/2006 | Morris et al. | ............... | 606/144 |
| 2002/0147456 | A1 | * | 10/2002 | Diduch et al. | ............... | 606/144 |
| 2003/0065337 | A1 | * | 4/2003 | Topper et al. | ............... | 606/144 |

FOREIGN PATENT DOCUMENTS

DE 42 35 602 A1 4/1994

OTHER PUBLICATIONS

Memorandum in Support of Defendant Surgical Solutions, LLC's Motion for Summary Judgment of Patent Invalidity; Case 1:03-cv-12310-NG; Document 55; filed Aug. 27, 2004; pp. 1-31.
Memorandum in Support of Defendant Surgical Solutions, LLC's Motion for Summary Judgment of Non-Infringement; Case 1:03-cv-12310-NG; Document 52; filed Aug. 27, 2004; pp. 1-35.

* cited by examiner

*Primary Examiner*—AnhTuan T Nguyen
*Assistant Examiner*—Tuan V Nguyen
(74) *Attorney, Agent, or Firm*—Dickstein Shapiro LLP (57) ABSTRACT

A suture passing instrument having a body housing a shape-memory wire, a jaw, a hand mechanism for articulating the jaw relative to a tip, an actuator, and a pusher for advancing the wire through the body and the tip. By actuating the hand mechanism, a surgeon may seize and maintain tissue with the jaw and the tip and, using the pusher, push a suture through the tissue.

5 Claims, 9 Drawing Sheets

SUTURE PASSING INSTRUMENT

This application claims the benefit of U.S. Provisional Application Ser. No. 60/380,302, filed May 15, 2002, the entire disclosure of which is incorporated by reference herein.

FIELD OF THE INVENTION

The present invention relates to surgical hand instruments and, more specifically, to a hand-held suture passing instrument for gripping and maintaining tissue to be sutured while a suture is advanced through the tissue.

BACKGROUND OF THE INVENTION

Both open and endoscopic surgical procedures often require sutures to ligate, join or otherwise treat tissue. Generally, suture needles with attached suture strands are grasped either manually or by forceps and passed through the desired work site so a knot can be tied. While the procedures are fairly uncomplicated in open surgery where most suture sites are readily accessible, in endoscopic procedures, where access to the work site is not readily available, the surgeon must use auxiliary devices to be able to grasp the suture strands and pass them through desired tissue.

Various instruments and techniques have been developed for surgical repairs requiring the passing of sutures to distant locations. For example, U.S. Pat. No. 4,781,190 to Lee discloses a two-ended needle enabling arthroscopic suturing of the interior of a joint. The two-ended needle of U.S. Pat. No. 4,781,190 may be either straight or curved and is provided with an eyelet intermediate the ends of the needle. The suture is passed through the eyelet of the needle and then through the tissue by alternately passing the ends of the needle through the tissue to be sutured. U.S. Pat. No. 4,441,497 to Paudler also discloses a suture passer having a plurality of flexible elongated members joined at their corresponding ends, the ends being sharpened enough to pass through desired tissue sites. Pushing the ends toward each other opens up spaces between the members into which one or more sutures may be placed. Moving the ends of the flexible members away from each other closes up the spaces to grip the sutures so that the ends of the flexible members and, consequently, the sutures, may be passed through desired suture sites.

Another device for advancing suture directly to a work site is described in U.S. Pat. No. 4,890,615 to Caspari et al., according to which a suture strand is advanced using a roller mechanism to feed the suture through a hollow needle at the end of an elongated tube into the tissue to be sutured. While suitable for mono-filament suture, such roller-type devices may unravel and disentangle multi-stranded suture.

Accordingly, there is a need for an improved suture passing instrument that overcomes the disadvantages of the prior art. A method of driving a length of suture through tissue to allow a stitch to be tied without removing a needle from the suture is also needed.

SUMMARY OF THE INVENTION

The present invention provides a suture passing instrument having a body, a jaw, a hand mechanism for articulating the jaw relative to a tip, an actuator and a pusher. A superelastic wire is loaded in the body and advanced through the body with the pusher. By actuating the hand mechanism, a surgeon may seize and maintain tissue with the jaw and the tip and, using the pusher, advance wire carrying a suture through the tissue.

These and other features and advantages of the invention will become apparent from the following detailed description that is provided in connection with the accompanying drawings and illustrated exemplary embodiments of the invention.

DETAILED DESCRIPTION OF THE PREFERRED EMBODIMENT

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The term "endoscopy" encompasses arthroscopy, laparoscopy, hysteroscopy, among others, and endoscopic surgery involves the performance of surgical procedures within a patient's body through small openings as opposed to conventional open surgery through large incisions.

Figures 1, 2, 3:
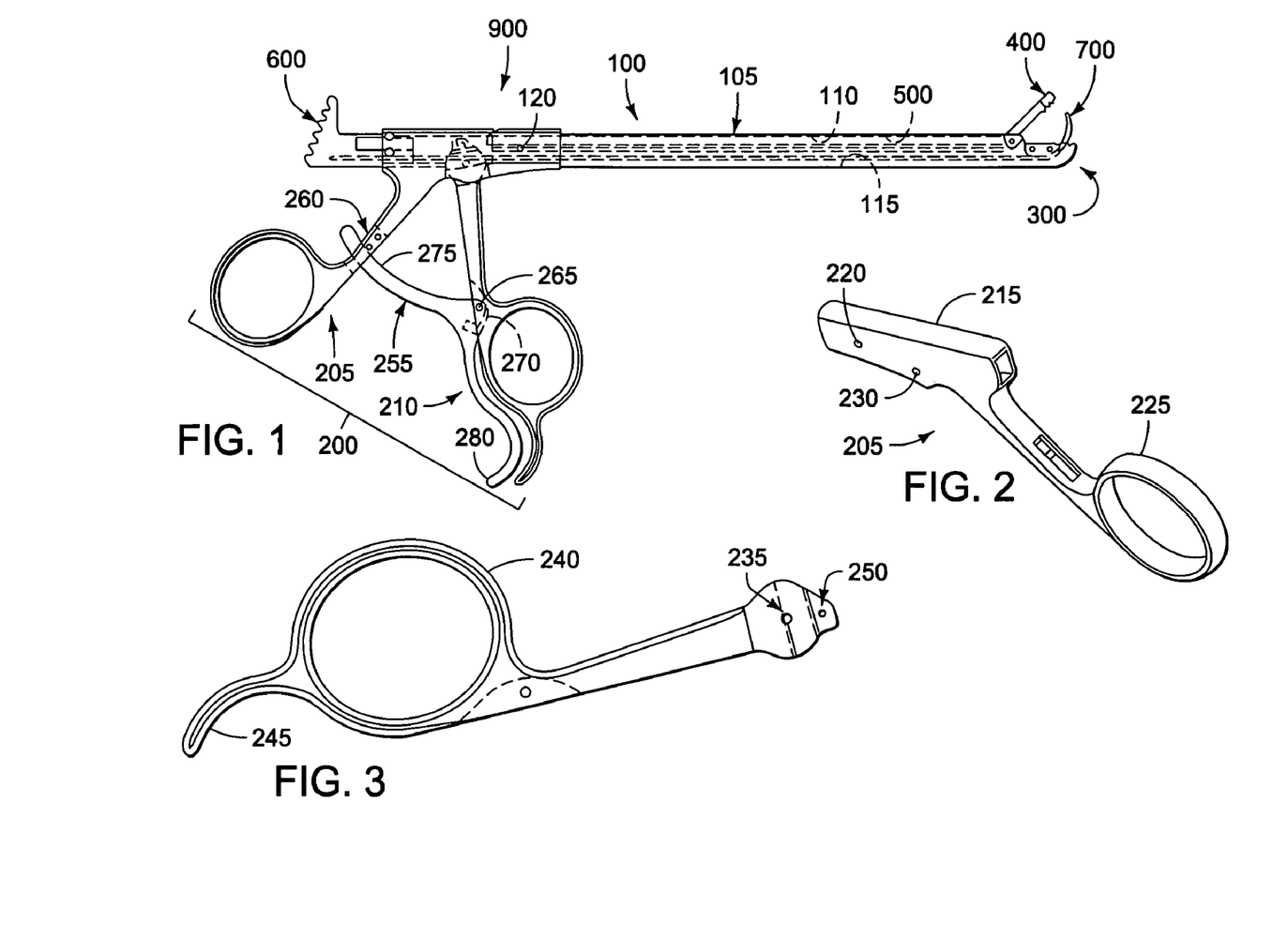
FIG. 1 is a side elevational view of the suture passing instrument and wire assembly of the present invention.
FIG. 2 is a distal side perspective view of the thumb arm of the embodiment of FIG. 1.
FIG. 3 is a side elevational view of the finger arm of the embodiment of FIG. 1.

Referring now to the drawings, where like elements are designated by like reference numerals, FIG. 1 illustrates a suture passing instrument or a suture pusher 900 of the present invention having an elongated tubular body 100, a hand mechanism 200, a tip 300, a jaw 400, an actuator 500 and a pusher 600. Hand mechanism 200 articulates jaw 400 relative to tip 300 with actuator 500. A superelastic wire 700 is loaded in body 100 and advanced through the body 100 with pusher 600. With hand mechanism 200, a surgeon may seize and maintain tissue with jaw 400 and tip 300 and, using pusher 600, advance wire 700 carrying a suture through the tissue, as described below.

Tube 100 is an elongated member 105 configured to be received in a trocar or cannula for accessing remote surgical sites accessed, for example, arthroscopically. Thus, the suture passing instrument 900 of the present invention is ideally suited for repairing rotator cuff tissue damage. Elongated member 105 has two axial throughbores 110 and 115. Throughbore 110 slidingly receives actuator 500. Actuator 500 is fairly stiff, therefore throughbore 110 need not be configured to closely receive actuator 500 to provide lateral support therefore. Throughbore 115 slidingly receives wire 700. As wire 700 is very flexible and requires lateral support, throughbore 115 is preferably configured to closely receive wire 700.

As illustrated in FIGS. 1-3, hand mechanism 200 includes two major sub-components: a thumb arm 205 and a finger arm 210. Thumb arm 205 includes an axial sleeve 215 that receives body 100. A first transverse throughbore 220 is in registry with a transverse throughbore 120 in body 100, both throughbores 120 and 220 receiving a pin for fixing body 100 thumb and arm 205 together. Thumb arm 205 is also provided with a second transverse throughbore 250 in registry with a transverse throughbore 235 of finger arm 210, as shown in FIG. 3. Throughbores 230 and 235 receive a pin for allowing pivoting of thumb arm 205 and finger arm 210. Thumb arm 205 also includes a thumb loop 225 for receiving a surgeon's thumb or otherwise grasping the present suture pusher.

Referring to FIG. 3, finger arm 210 has a finger loop 240 for receiving a surgeon's finger or otherwise grasping the present suture pusher. Finger arm 210 also has a finger hook 245 on which a surgeon may rest a finger or otherwise manipulate the present suture pusher. Finger arm 210 is also provided with an eccentric throughbore 250 which receives a pin for urging translation of actuator 500, as described below.

Finger arm 210 includes a ratchet 255 pivotably mounted on a pivot pin 265. The ratchet 255 has a plurality of teeth 275. Thumb arm 205 includes a block 260 having teeth extending toward teeth 275. As ratchet 255 is biased toward block 260, when thumb and finger arms 210 and 205 are squeezed together, teeth 275 slide over the teeth of block 260. When thumb and finger arms 210 and 205 are released, teeth 275 engage the teeth of block 260 to prevent separation of thumb and finger arms 210 and 205. Thus, a surgeon may squeeze thumb and finger arms 210 and 205 together and increase clamping force imparted by jaw 400 against tip 300. Upon release, ratchet 255 and block 260 lock together to maintain the clamping force until finger release lever 280 is actuated, rotating ratchet 255 away from block 260 and disengaging teeth 275 from the teeth of block 260.

Figure 4:
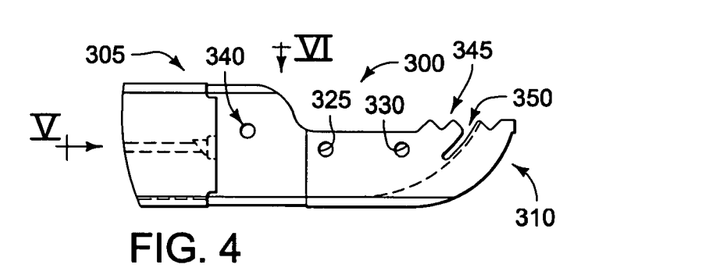
FIG. 4 is a side elevational view, drawn to an enlarged scale, of the distal tip of the embodiment of FIG. 1.
Figure 5:
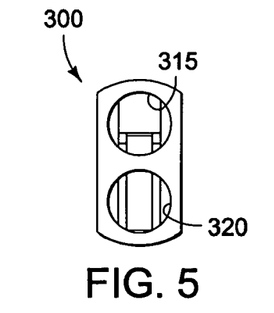
FIG. 5 is a distal view of the embodiment of FIG. 4, drawn from the perspective of line V in FIG. 4.
Figure 6:
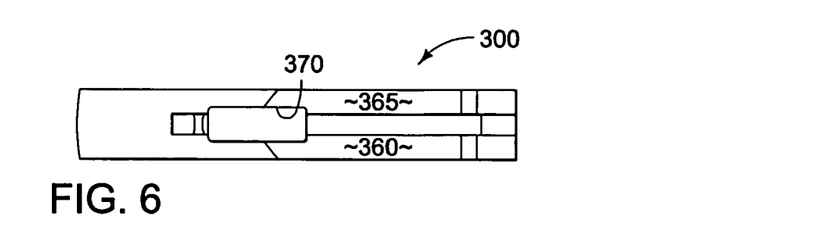
FIG. 6 is a side elevational view of the embodiment of FIG. 4 drawn from the perspective of line VI in FIG. 4.

Referring to FIGS. 4-6, tip 300 is preferably formed integrally with body 100 and has a proximal end 305 and a distal end 310. As shown in FIG. 5, proximal end 305 has two axial bores 315 and 320. Axial bore 315 receives actuator 500. Axial bore 320 receives wire 700. As also shown in FIG. 6, the tip 300 has cavity 370, axial walls 360 and 365 for guiding wire 700 and maintaining axial alignment thereof with body 100 during advancement of wire 700 through tip 300.

Referring to FIGS. 4-6, tip 300 is preferably formed integrally with body 100 and has a proximal end 305 and a distal end 310. As shown in FIG. 5, proximal end 305 has two axial bores 315 and 320. Axial bore 315 receives actuator 500. Axial bore 320 receives wire 700. As also shown in FIG. 6, the tip 300 has axial walls 360 and 365 for guiding wire 700 and maintaining axial alignment thereof with body 100 during advancement of wire 700 through tip 300.

Figures 7, 8, 9:
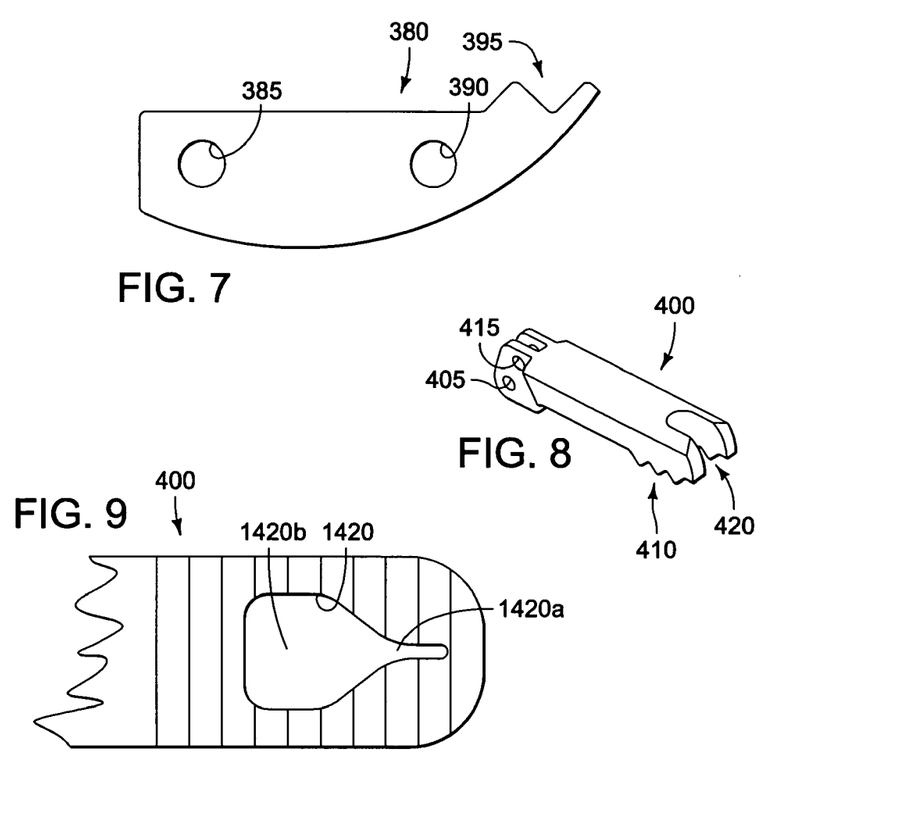
FIG. 7 is a side elevational view, drawn to an enlarged scale, of the slot plug of the embodiment of FIG. 1.
FIG. 8 is a distal side perspective view, drawn to an enlarged scale, of the jaw of the embodiment of FIG. 1.
FIG. 9 is a side elevational view of an alternative embodiment of the jaw of the embodiment of FIG. 1.

Reference is now made to FIG. 7. Tip 300 has a pair transverse axial throughbores 325 and 330 that respectively register with transverse throughbores 385 and 390 in a slot plug 380 for mounting slot plug 380 to tip 300. Slot plug 380 has an arcuate inner surface 395 for guiding wire 700 relative to tip 300 through tissue. In operation, when initially advancing wire 700 from body 100, axial walls 360, 365 and arcuate inner surface 395 cooperatively guide wire 700 axially. When wire 700 reaches inner arcuate surface 395, walls 360, 365 and inner arcuate surface 395 guide wire 700 in the plane corresponding to axial walls 360, 365 increasingly orthogonally relative to body 100 as wire 700 advances.

As illustrated in FIG. 4 and FIG. 8, tip 300 has another transverse throughbore 340 which is in registry with throughbore 405 in jaw 400 for pivotally mounting jaw 400 with respect to tip 300. Both tip 300 and jaw 400 have teeth 345 and 410, respectively, which come into registry when jaw 400 is articulated into a closed position with respect to tip 300 for seizing and maintaining tissue between jaw 400 and tip 300, as described below.

Tip 300 has an arcuate slot 350 for receiving suture. Slot 350 is aligned with arcuate inner surface 395 of slot plug 380 so as to position a suture received in slot 350 with respect to wire 700, as described below.

Jaw 400 of FIG. 4 has a transverse throughbore 415 for receiving a pin for connecting jaw 400 to actuator 500, as shown in FIG. 1. Jaw 400 is also provided with a distal transverse opening 420 which is positioned relative to arcuate inner surface 395 of slot plug 380 so that wire 700 passes therethrough. As shown, the first embodiment of transverse opening 420 is an open slot. An open slot allows the present suture pusher to be withdrawn from tissue through which a suture has been pushed without entangling the suture pushed through the tissue, as described below.

FIG. 9 illustrates a second embodiment of a distal transverse opening 1420 shown having a generally tear drop shape. Narrow portion 1420a of hole 1420 is distal of wider portion 1420b. This configuration and orientation of opening 1420 permits a surgeon to capture or cleat suture received through opening 1420 upon withdrawal of the present suture pusher from the tissue through which a suture has been pushed and the wire retracted, as described below.

Referring again to FIG. 1 and FIG. 10, actuator 500 has a proximal end 505 and a distal end 510. Proximal end 505 has a transverse throughbore 515 which registers with throughbore 250 of finger arm 210, as shown in FIG. 3. A pin received through throughbores 250 and 515 provides for pivotal connection between actuator 500 and finger arm 210. Articulating finger arm 210 relative to thumb arm 205 causes actuator 500 to translate relative to body 100.

Figure 10:
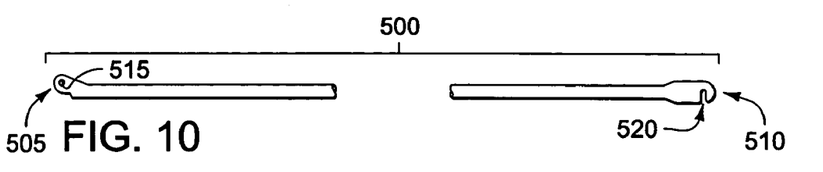
FIG. 10 is a side elevational view of the actuator of the embodiment of FIG. 1.

Distal end 510 of actuator 500 has a slot 520 which comes into registry with throughbore 415 of the jaw 400, as shown in FIG. 8. A pin received in throughbore 415 and slot 520 provides for pivotal, sliding connection between actuator 500 and jaw 400. When actuator 500 is translated relative to body 100, the walls of slot 520 urge the pin to rotate jaw 400 relative to throughbore 405. As jaw 400 rotates, the position of throughbore 415, hence the pin, changes laterally relative to actuator 500. Thus, the pin translates laterally within slot 520 as jaw 400 rotates relative to tip 300.

Figure 11:
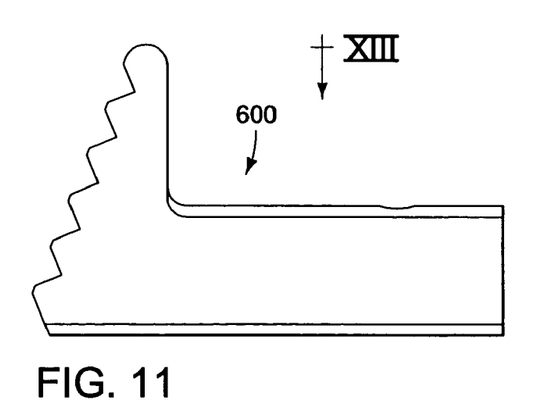
FIG. 11 is a side elevational view, drawn to an enlarged scale, of the pusher of the embodiment of FIG. 1.
Figure 12:
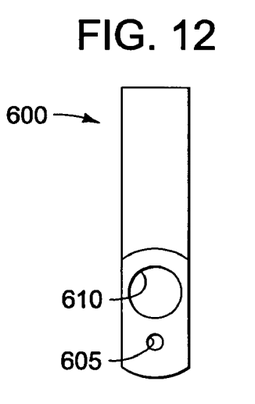
FIG. 12 is a proximal view of the embodiment of FIG. 11.
Figure 13:
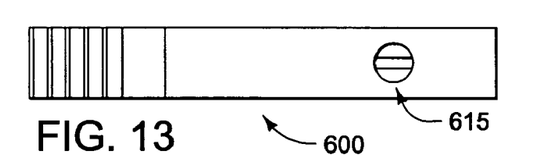
FIG. 13 is a side elevational view of the embodiment of FIG. 11, drawn from the perspective of line XIII in FIG. 11.

Referring again to FIG. 1 and FIG. 11, pusher 600 is slidingly received in the proximal end of sleeve 215 of thumb arm 205. As shown in FIG. 12, pusher 600 has an axial bore 605 for receiving wire 700. As shown in FIG. 13, a transverse screw 615 fixes wire 700 in axial bore 605. Pusher 600 has another axial bore 610 for receiving a spring for biasing pusher 600 away from thumb arm 205.

Figure 14:
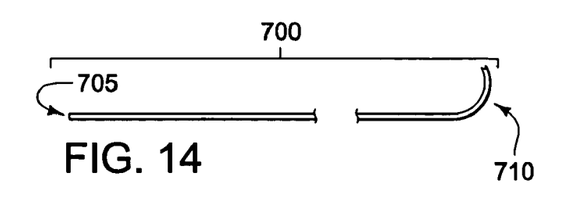
FIG. 14 is a side elevational view of the wire of the embodiment of FIG. 1.

Referring now to FIG. 14, wire 700 has a proximal end 705 and a distal end 710. Wire 700 is preferably constructed from nitinol, or other shape-memory material consistent with the principles of the invention. Distal end 710 is formed so that, in a free state, distal end 710 has an arcuate shape. In practice, when wire 700 is installed in the present suture pusher and fixed relative to pusher 600, when pusher 600 is drawn back from thumb arm 205, arcuately-shaped distal end 710 is drawn into generally linear passage 115 in body 100, temporarily forcing distal end 710 to assume a generally linear shape. When a surgeon pushes on pusher 600 to urge wire 700 back out of tip 300, as distal end 710 of wire 700 advances, distal end 710 regains the arcuate shape. This permits the surgeon to execute generally transverse stitching relative to tissue in a remote surgical site with a suture pusher which assumes a very slim profile. Thus, the present invention permits access to and repair of tissue which otherwise would not be repairable without more invasive or traumatic surgical procedures.

Figure 15:
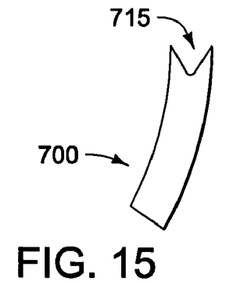
FIG. 15 is a side elevational view, drawn to an enlarged scale, of the distal end of the embodiment of FIG. 14.

Wire 700 (FIG. 15) is provided with a notch 715 at its tip for retaining suture to ensure that the suture is urged through tissue as the wire is pushed therethrough.

The present invention provides a method for using the above-described suture passing instrument 900 for suturing tissue. The suture passing instrument of the present invention, described above with reference to FIGS. 1-15, may be employed in various surgical medical procedures for advancing the suture in the proximity of a surgical site, and for employing the suture with a cannulated instrument during such surgical procedures. For example, the suture passing instrument may be employed in endoscopic and arthroscopic procedures, including but not limited to arthroscopic rotator cuff repair, Bankhart shoulder repair, meniscal repair, and any orthopaedic procedure that requires tying a knot through soft tissue or bone tunnels, for example, or in conjunction with fixation devices, such as suture anchors. Additionally, the suture passing instrument may be utilized in other general surgical and specialty procedures that require suturing at a remote site, such as inside the body. The suture passing instrument of the present invention may be also used in repairs where suture visibility or finger access can be limited.

It will be appreciated, of course, that while the suture passing instrument may be particularly useful for performing remote procedures through access sheaths, trocars and cannulated surgical instruments, it will also find use in open surgical procedures.

Figure 16:
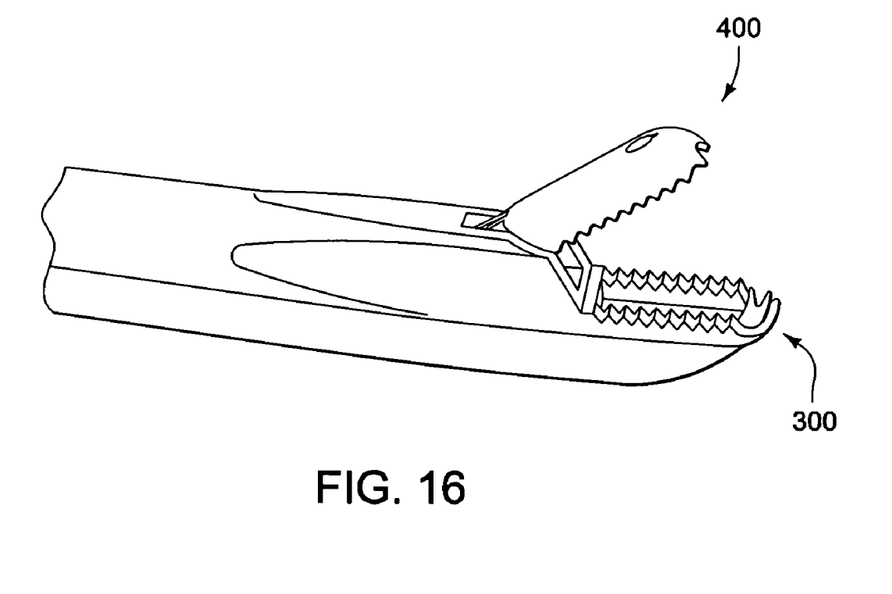
FIG. 16 is a side perspective view of a distal end of the embodiment of FIG. 1.
Figure 17:
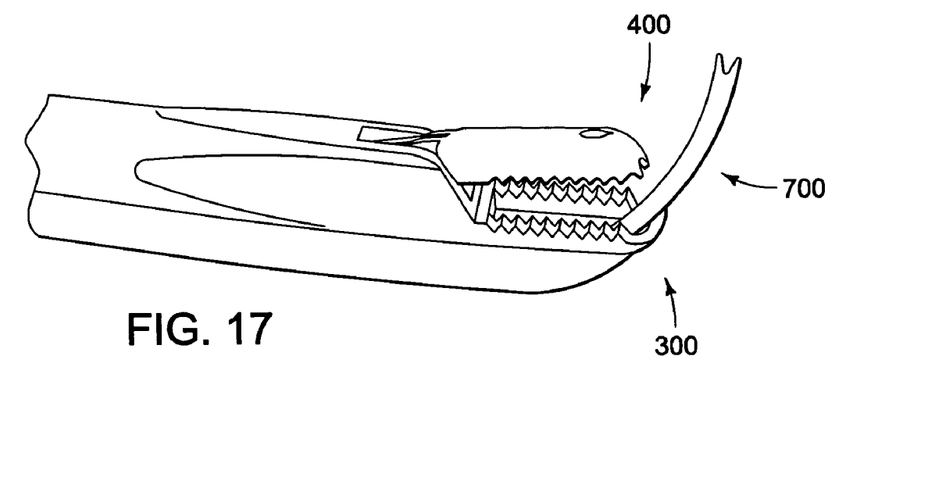
FIG. 17 is a side perspective view of the embodiment of FIG. 1 with the wire advanced therefrom.

Referring now to FIG. 16, suture passing instrument 900 is prepared for use by first manipulating hand mechanism 200 to articulate jaw 400 relative to tip 300 into a generally opened configuration, as shown. The surgeon then loads wire 700, guided by inner arcuate surface 395 of slot plug 380, into axial bore 115 of body 100, as shown in FIG. 17. Proximal end 705 of wire 700 is received in axial bore 605 of pusher 600 and fixed relative thereto with transverse screw 615. Once wire 700 is fixed to pusher 600, pusher 600 is drawn proximately relative to thumb arm 205, retracting wire 700 into axial bore 115 and away from tip 300.

Figure 18:
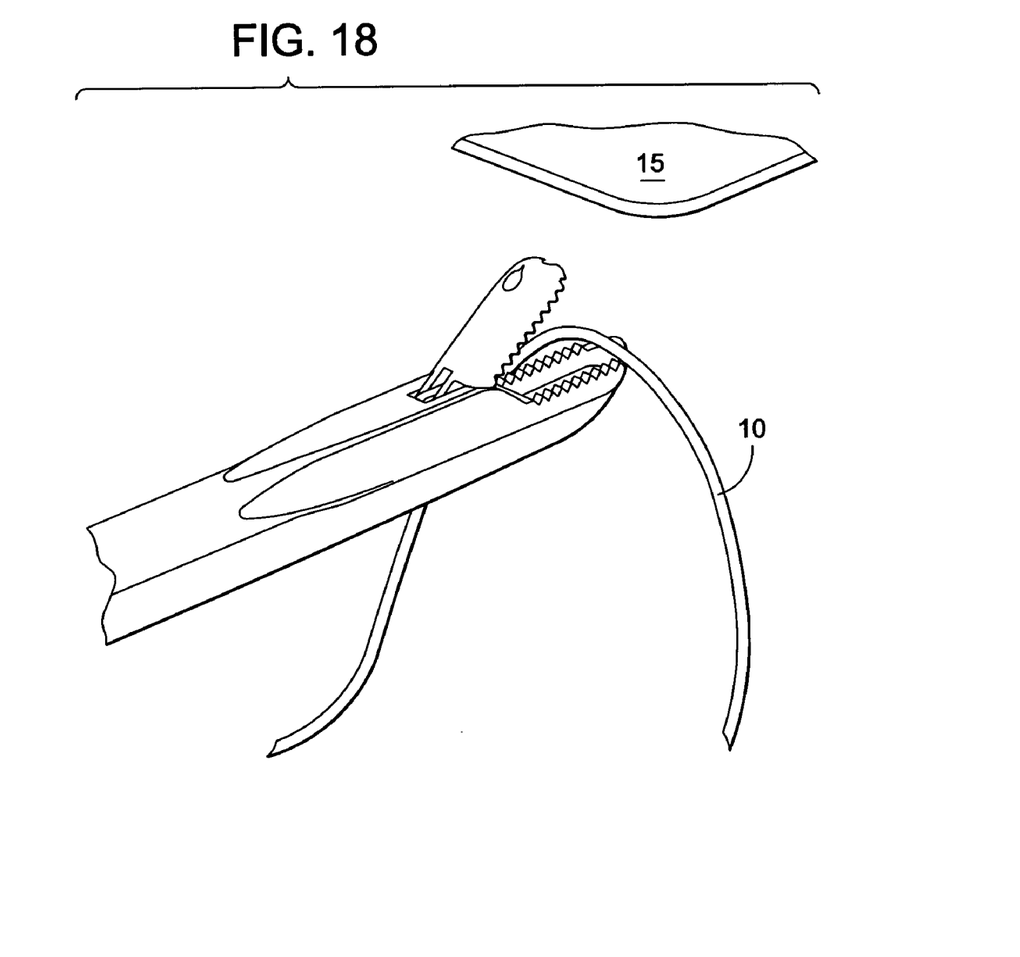
FIG. 18 is a side perspective view of the embodiment of FIG. 1 with suture disposed on a jaw thereof
Figure 20:
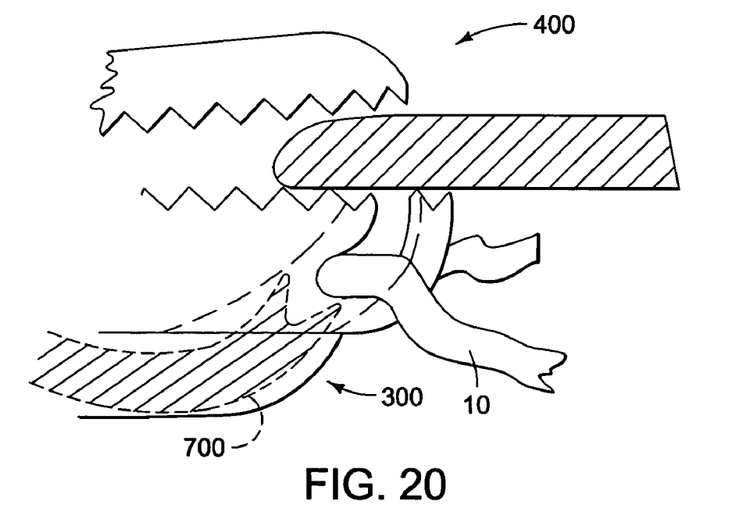
FIG. 20 is a schematic side view of the embodiment of FIG. 19.

Subsequently, a suture 10 is placed in slot 350 of tip 300, as shown in FIG. 20. The distal end of the present suture passing instrument may be advanced in a trocar or cannula proximate to tissue 15 to be sutured at a remote surgical site, as illustrated in FIG. 18.

Figure 19:
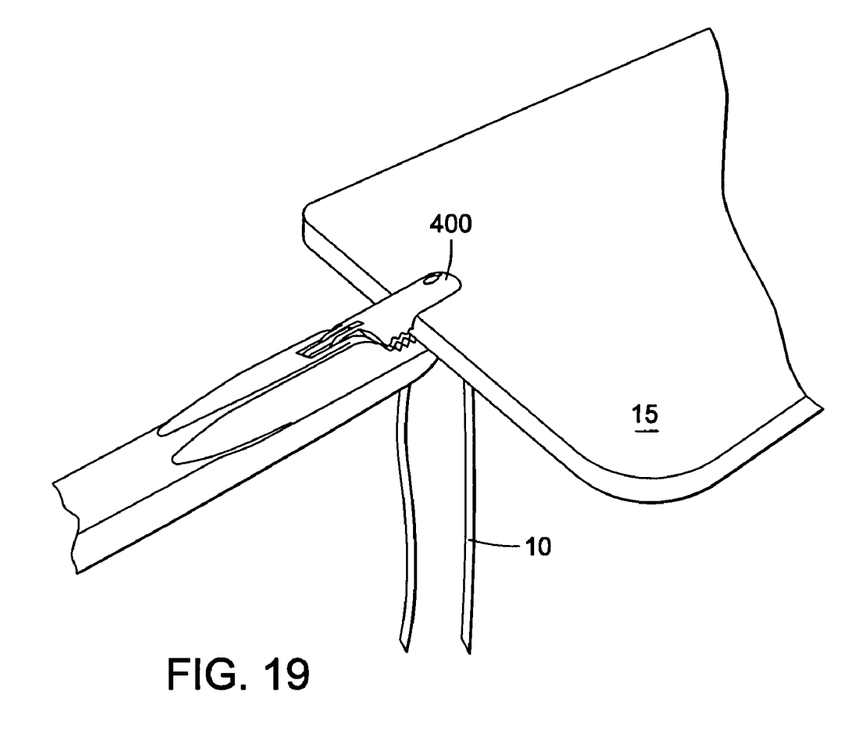
FIG. 19 is an environmental perspective view of the embodiment of FIG. 17 with the jaw articulated against the tip thereof to grasp tissue.

Referring to FIGS. 19 and 20, the surgeon manipulates hand mechanism 200 to articulate jaw 400 relative to tip 300 to seize tissue 15. Ideally, slot 350 and inner arcuate surface 395 position suture 10 and wire 700, respectively, so that suture 10 may be pushed through tissue 15 leaving appropriate spacing with respect to the edge of tissue 15 so that suture 10 does not tear from tissue 15.

Figure 21:
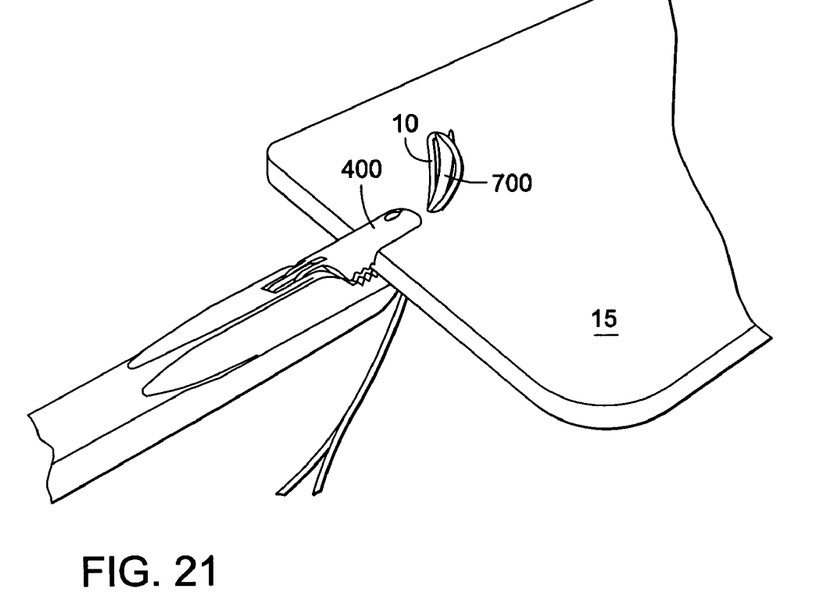
FIG. 21 is an environmental perspective view of the embodiment of FIG. 19 with the wire having urged suture through tissue.
Figure 22:
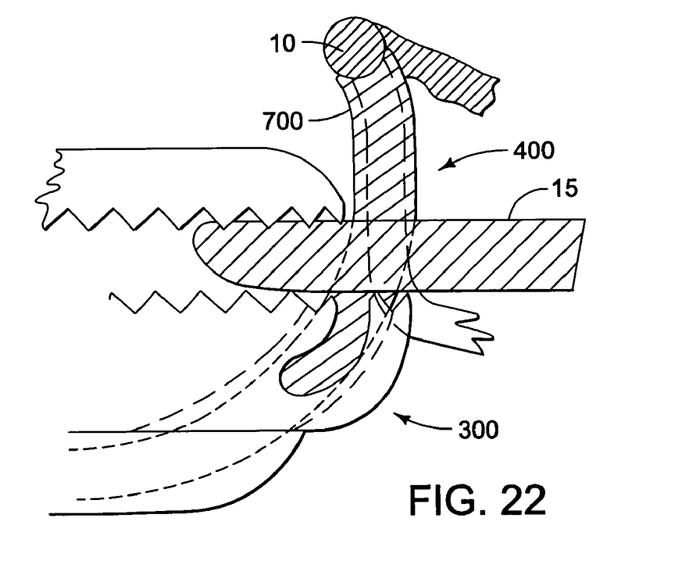
FIG. 22 is a schematic view of the embodiment of FIG. 21.

Referring to FIGS. 21 and 22, the surgeon next advances pusher 600 of the suture passing instrument 900 to urge wire 700 to push suture 10 through tissue 15. Either embodiment of transverse opening 420 or 1420 of jaw 400 provides appropriate backing against tissue 15 locally to where wire 700 is pushed through tissue 15, to facilitate wire penetration of tissue 15 without residual tears therethrough emanating from the puncture site.

Figure 23:
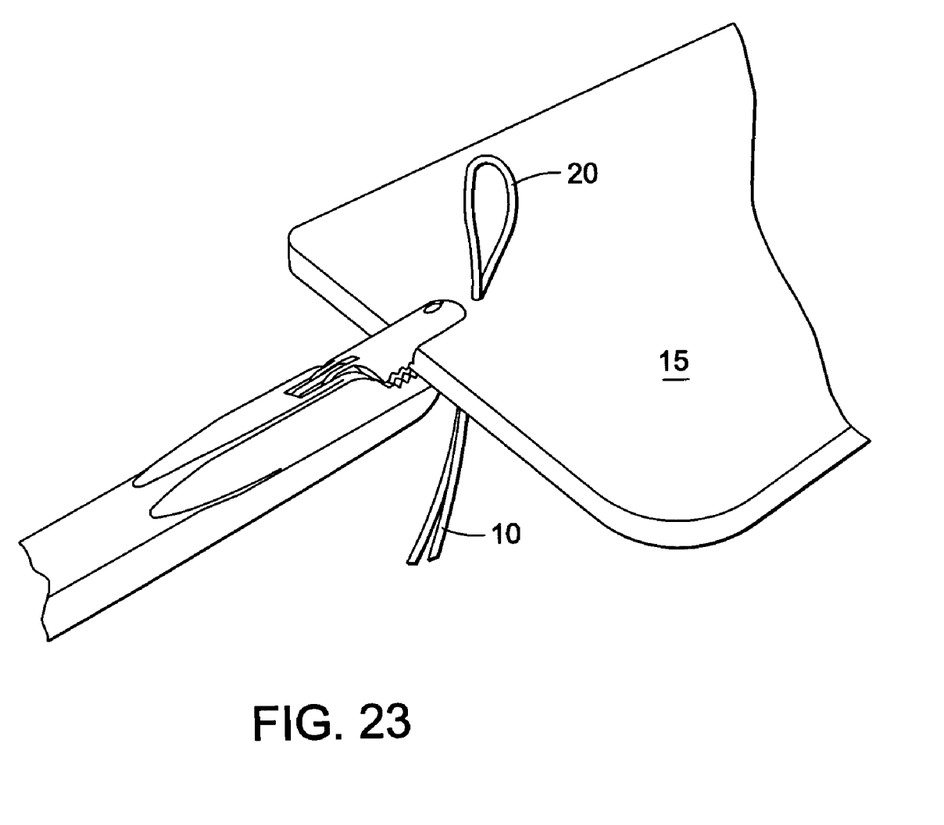
FIG. 23 is an environmental perspective view of the embodiment of FIG. 21, with the wire withdrawn, leaving a loop of suture in the tissue.

Referring to FIG. 23, the surgeon next withdraws wire 700 leaving a loop 20 of suture 10 in tissue 15. Once wire 700 is withdrawn, jaw 400 may be articulated away from tip 300, as shown in FIG. 16, to release tissue 15 and withdraw the present suture pusher from tissue 15, leaving suture loop 20 therethrough.

Figure 24:
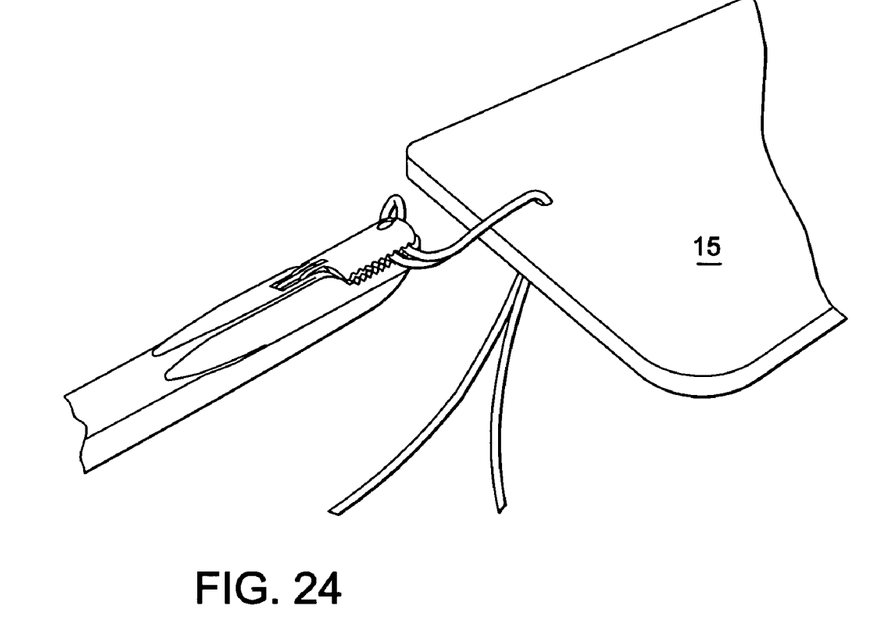
FIG. 24 is an environmental perspective view of the embodiment of FIG. 23, the jaws of the present suture passing instrument having grasped the loop of suture.
Figure 25:
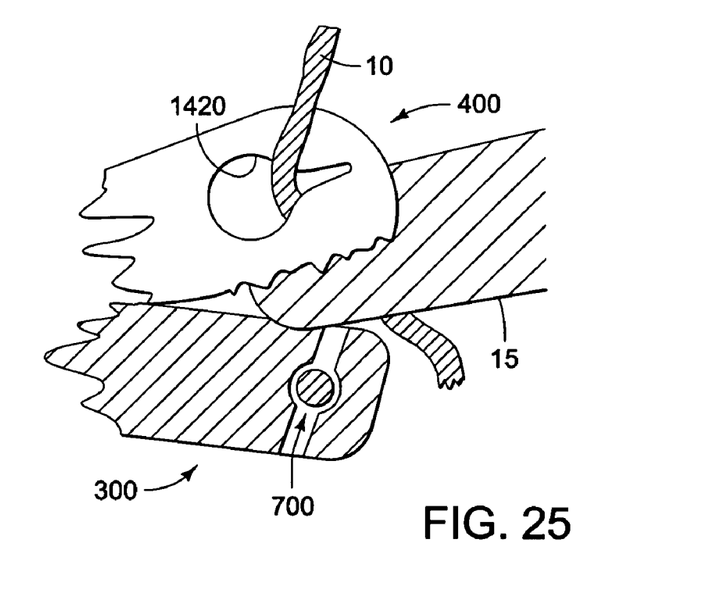
FIG. 25 is a schematic environmental perspective view of the embodiment of FIG. 24.

Referring to FIG. 24, the jaws of the suture passing instrument of the present invention (or another suture retriever instrument) then may be used to seize suture loop 20, similar to seizing tissue 15, as described above, to pull suture 10 through tissue 15. Alternatively, and referring to FIG. 25, if jaw 400 is provided with tear drop-shaped distal opening 1420 (FIG. 9), the surgeon may withdraw the present suture passing instrument and snag or cleat suture 10 to pull suture 10 through tissue 15.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A suture passing instrument, comprising:
an elongated tubular member having a proximal end and a distal end, the tubular member comprising a first axial throughbore and a second axial throughbore;
a wire received in the first axial throughbore of the elongated tubular member, the wire being formed of a shape-memory material and having a distal end formed, so that, as the distal end of the wire passes through a linear throughbore it assumes a straight shape, whereas, in a free state, the distal end of the wire has an arcuate shape;
a tip provided at the distal end of the tubular member and integral with the tubular member, the tip including at least one axial bore in communication with the first axial throughbore of the tubular member for receiving the wire, the tip further comprising a slot formed within a body of the tip, the slot having a configuration for receiving a strand of suture and for positioning the strand of suture in the path of the wire, such that, as the wire is advanced through the axial bore of the tip and exits distally into the slot, the suture is engaged by a central portion of the most distal end of the wire, and the distal end of the wire, with the engaged suture, regains its arcuate shape to facilitate transverse stitching of tissue;

a jaw pivotable with respect to the tip, the jaw comprising a distal opening aligned with the axial bore of the tip for receiving the wire therein, the distal opening of the jaw being an open slot extending to a most distal end of the jaw; and a pusher provided at the proximal end of the tubular member, a proximal end of the wire being coupled to the pusher such that the pusher can be used to advance and retract the distal end of the wire from the tip.

2. The suture passing instrument of claim 1, wherein the slot is arcuate.

3. The suture passing instrument of claim 1, wherein the jaw further comprises a plurality of teeth for gripping tissue.

4. The suture passing instrument of claim 1, wherein the wire is superelastic.

5. The suture passing instrument of claim 4, wherein the wire is a nitinol wire.

* * * * *

UNITED STATES PATENT AND TRADEMARK OFFICE
CERTIFICATE OF CORRECTION

PATENT NO. : 7,585,305 B2 Page 1 of 1
APPLICATION NO. : 10/428072
DATED : September 8, 2009
INVENTOR(S) : Peter J. Dreyfuss It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 593 days.

Signed and Sealed this

Fourteenth Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,585,305 B2 | Page 1 of 1 |
| APPLICATION NO. | : 10/428072 | |
| DATED | : September 8, 2009 | |
| INVENTOR(S) | : Dreyfuss et al. | |

It is certified that error appears in the above-identified patent and that said Letters Patent is hereby corrected as shown below:

Title Page, Item (75) Inventor, should read

--(75) Inventors: Peter J. Dreyfuss, Naples, FL (US); Stephen S. Burkhart, Boerne, TX (US)--.

Signed and Sealed this
Nineteenth Day of April, 2016

Michelle K. Lee
*Director of the United States Patent and Trademark Office*